United States Patent [19]
Krauter et al.

[11] Patent Number: 6,013,026
[45] Date of Patent: Jan. 11, 2000

[54] RELEASABLE LARYNGEAL BLADE ASSEMBLY AND SET OF LARYNGOSCOPES

[75] Inventors: Allan I. Krauter, Skaneateles; Catherine R. Wojnowicz, Auburn; Michael T. Turner, Marcellus; Bernd F. Koehler, Liverpool; Raymond A. Lia, Auburn; James J. O'Brien, Marcellus; Francis Cichostepski, Skaneateles; Michael T. Cerio, Marcellus; Robert Vivenzio, Auburn, all of N.Y.

[73] Assignee: Welch Allyn, Inc., Skaneateles, N.Y.

[21] Appl. No.: 09/257,762

[22] Filed: Feb. 25, 1999

[51] Int. Cl.[7] ........................................................ A61B 1/26
[52] U.S. Cl. ............................................ 600/193; 600/199
[58] Field of Search .................................... 600/185, 193, 600/190, 199

[56] References Cited

U.S. PATENT DOCUMENTS

4,958,624  9/1990  Stone et al. .
5,060,633  10/1991  Gibson ..................................... 600/193
5,529,570  6/1996  Storz ..................................... 600/185 X

*Primary Examiner*—Jeffrey A. Smith
*Attorney, Agent, or Firm*—Wall Marjama Bilinski & Burr

[57] ABSTRACT

A laryngeal blade assembly includes a light pipe assembly attached to a blade having a light pipe disposed along a major dimension of the blade. The light pipe assembly is releasably attached to the blade in a non-axial direction in relation to the major dimension, wherein said light pipe assembly can be released from the blade without the aid of tools. The light pipe assembly includes a supporting block for fixedly retaining the light pipe. The supporting block has a bore disposed in a non-axial direction to the major dimension of the blade. A non-axial member fixedly attached to the blade and sized for engaging the bore includes an undercut portion. An annular engagement member is fitted within said undercut portion for engaging the bore to allow the release of the light pipe assembly when a predetermined holding force is exceeded.

16 Claims, 8 Drawing Sheets

RELEASABLE LARYNGEAL BLADE ASSEMBLY AND SET OF LARYNGOSCOPES

FIELD OF THE INVENTION

This invention relates to the field of laryngoscopes and particularly to a hand-held laryngoscope having a removable and interchangeable blade assembly.

BACKGROUND OF THE INVENTION

Laryngoscopes are hand-held examination instruments which are used to displace the tongue and epiglottis to permit a direct view of the larynx, in the introduction and insertion of tracheal tubes in the trachea during intubation narcosis and other life threatening situations.

Most laryngoscopes consist of a handle containing a battery power source. A pivotable laryngeal blade assembly extends from the handle, the blade being movable so as to fold flat against the handle for storage or to a deployed position for use. Furthermore, the blade assembly is completely detachable from the handle.

Several types of laryngoscopes are known. In one version, the handle interior contains a lamp and a series of optical fibers in a light pipe to guide illumination to the distal end of the blade. In a separate other version, the lamp is provided at the end of the light pipe. In each version, the light pipe is attached to the blade.

It is desirable that the light pipe assembly be removed from the blade to allow for cleaning, disinfecting and sterilizing.

It is a desire to provide capability for removing the light pipe assembly from the blade without the use of tools. U.S. Pat. No. 4,958,624 to Stone et al., incorporated herein by reference in its entirety, describes a removable screw for securing the light pipe assembly to the mounting blade. A tool, such as a screwdriver, is required to remove the screw and release the light pipe assembly from the blade. However, this removal procedure is both tedious and time consuming.

Another known instrument that is commercially available through Heine, Inc. of Germany includes a laryngeal blade having a light pipe assembly which releasably slides into the blade in an axial direction; that is, along the major direction. A problem with this design is that the light pipe assembly may be ejected prematurely from the blade due to a sudden impact (even when assembled to handle), such as might occur if one were to inadvertently drop or knock the instrument. Because of the urgency of use of such instruments in an operating theater, emergency room or other location, an inadvertent release of the light pipe assembly is not desired.

SUMMARY OF THE INVENTION

Therefore, it is an object of the present invention to provide a laryngeal blade assembly that overcomes the above-described deficiencies of the prior art.

It is another object of the present invention to provide a laryngeal blade assembly having a light pipe assembly which is easily detachable from the remainder of the blade assembly without the use of tools.

It is a further object of the present invention to provide a light pipe assembly which allows selective detachment from the blade assembly but in which the light pipe assembly remains secure to the blade and handle when dropped or subjected to a sudden impact.

It is another object of the present invention to provide a laryngeal blade that can be used with both an incandescent and a fiber optic light pipe assembly.

Therefore and according to a preferred aspect of the invention, there is provided a laryngoscope blade assembly comprising a laryngeal blade configured for viewing the larynx of a patient, a light pipe assembly attached to said blade and disposed in an insertion direction along the major dimension of said blade, and means for releasably attaching said light pipe assembly to said blade, such that said light pipe can be non-axially removed from said blade without the aid of tools.

The light pipe assembly includes a supporting block for fixedly retaining a light pipe, said block having a bore disposed in a non-axial direction to said major dimension, and in which said releasable attachment means includes a non-axial member fixedly attached to said blade and sized for engaging said bore. The non-axial member includes a shaft having an undercut portion, and an annular engagement member fitted within said undercut portion for engaging said bore to allow release of said light pipe assembly when a predetermined release force applied along the axis of said bore is exceeded.

These and other objects, advantages, and features will be described in the following Detailed Description of the Invention which should be read in conjunction with the accompanying drawings.

DETAILED DESCRIPTION OF THE INVENTION

Before discussing that which Applicant regards as the main feature of the present invention, a discussion of the two types of laryngoscopes are provided for background purposes. In brief, the first type of laryngoscope includes a fiberoptic light pipe assembly, while the second type of laryngoscope includes a light pipe assembly and a lamp. Each laryngoscope commonly consists of a handle and a laryngeal blade assembly. The handle of one type of laryngoscope, however, is not interchangeable with the handle of the second type of laryngoscope.

Figures 1, 2, 8:
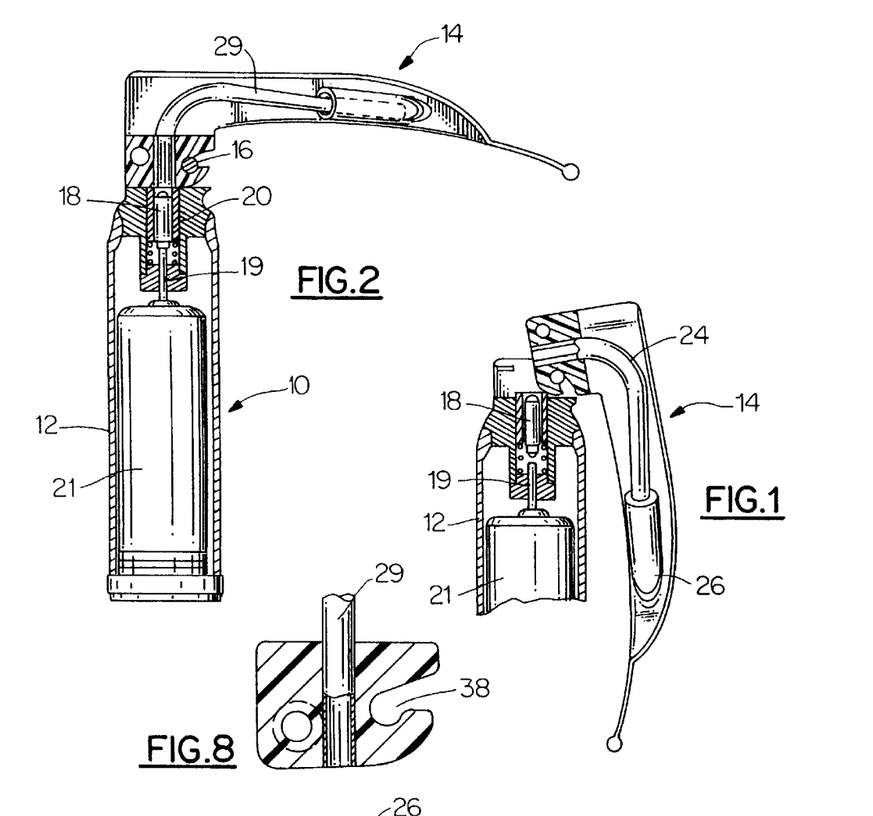
FIG. 1 is a partial sectional view of a fiber optic laryngoscope having a pivotable blade assembly in accordance with the present invention, the blade being shown in a folded position.
FIG. 2 is a sectional view of the laryngoscope of FIG. 1 in a deployed or use position.
FIG. 8 is a cross sectional view through the supporting block of FIG. 3.

Referring to FIGS. 1 and 2, the fiber optic laryngoscope 10 includes a handle 12, a laryngeal blade assembly 14 mounted on handle 12 about a pin 16 and held in the operative position (FIG. 2) by a latch (not shown). Slidably mounted in a tube 20 provided in the upper portion of handle 12 is a miniature lamp 18 which is released from a battery contact 19 by moving blade assembly 14 into the folded position of FIG. 1, thereby causing lamp 18 to de-energize. In order to energize lamp 18, blade assembly 14 is moved to its operating position which depresses lamp 18 to battery contact 19. Details relating the interrelations between the handles and the blade assemblies can be found in U.S. Pat. No. 4,958,624 to Stone et al. previously incorporated above in its entirety.

Figure 3:
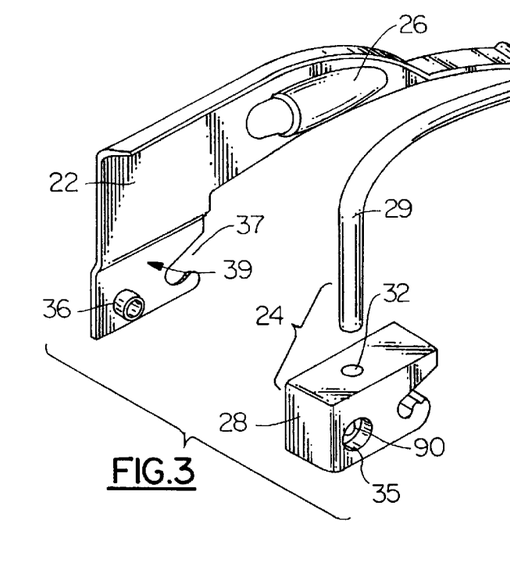
FIG. 3 is an exploded perspective view of the laryngeal blade assembly of FIGS. 1 and 2.
Figure 4:
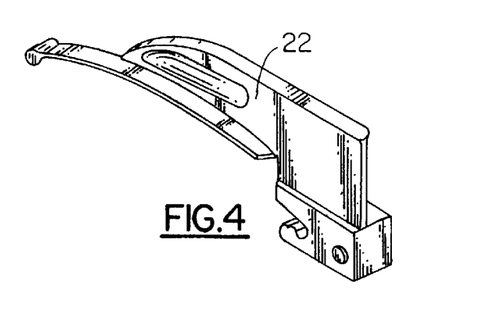
FIG. 4 is a rear perspective view of the blade assembly of the present invention.

Referring to FIGS. 1, 3 and 4, the blade assembly 14 consists of a blade 22, sometimes referred to as a spatula and usually made from a stainless steel or other easily sterilized material, and a fiber optic light pipe assembly 24 mounted in a pocket or cavity 26 formed in an interior wall of the blade 22 and secured thereto by a screw assembly 31. FIG. 4 shows a perspective view of the back side of blade 22.

Light pipe assembly 24 consists of a light pipe 29 and a supporting block 28 formed into a unitary sub-assembly, shown exploded in FIG. 3. Light pipe 29 is bent into a generally right angle shape and is hollow so as to contain a plurality of optical fibers used to transmit light from the lamp 18 to the distal end of the light pipe 29.

The supporting block 28 has a non-axial bore 32 extending through a top surface thereof to fixedly receive one end of pipe 29 and another non-axial bore 35 orthogonal relative to the bore 32 arranged along axis 99 to receive screw assembly 31. Bore 35 has an internal boss or annular rim portion 90. Screw assembly 31 is inserted through bore 35 in block 28 into a threaded portion 36 provided on a base portion 39 of the blade 22. The blade 22 includes the base portion 39 and an elongated tongue portion extending on one end therefrom. A slot 37 is cut into the base portion 39 of blade 22 to fit over pin 16 of handle 12. Slot 37 in blade 22 is a "universal" slot compared to slot 38 of supporting block 28. Slot 38 of supporting block 28, shown in FIG. 8, is designed to engage pin 16 and provide the necessary mutually exclusive attachment function with pin 16 of handle 12.

Figures 5, 6, 7:
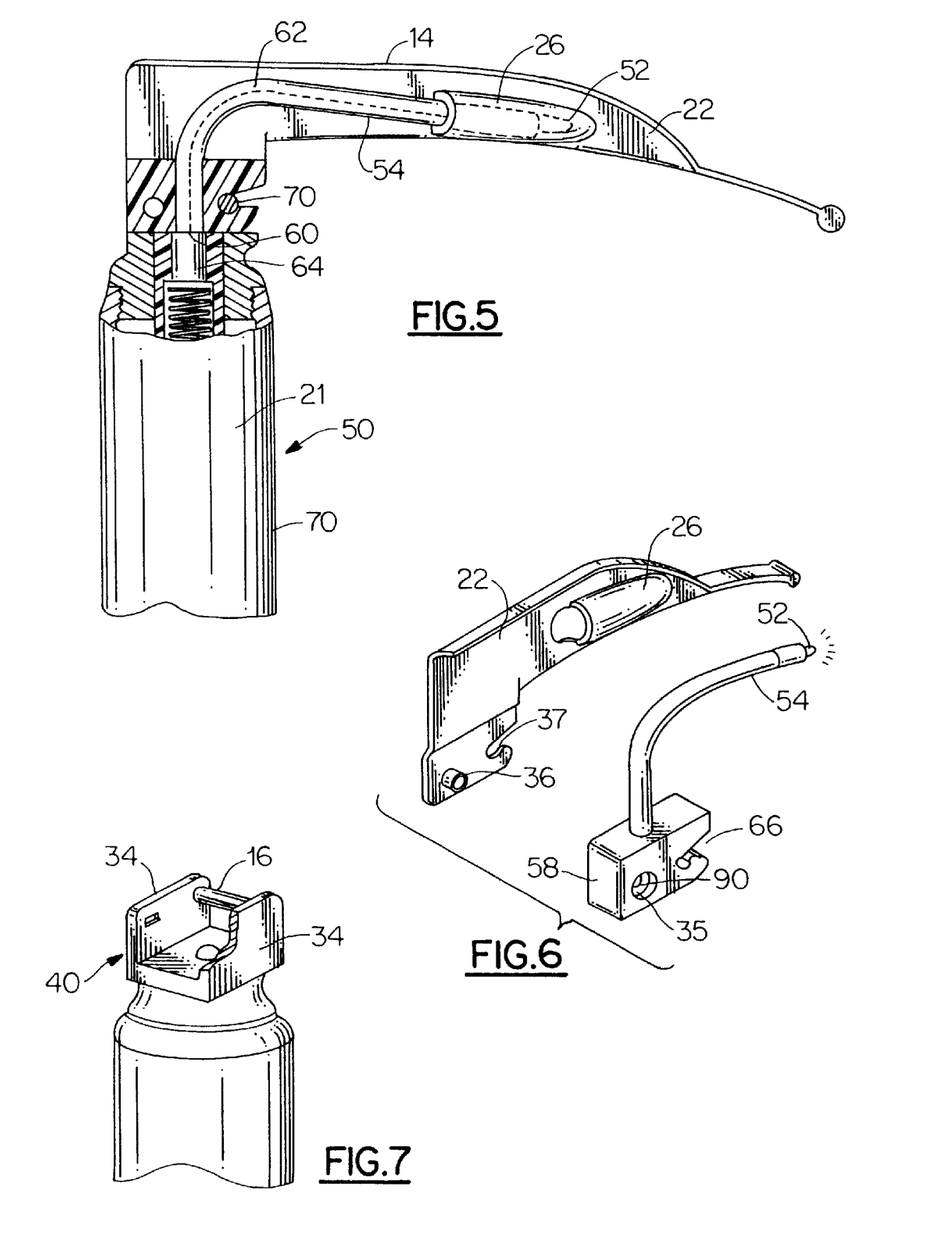
FIG. 5 is a partial sectional view of a conventional, standard lamp type laryngoscope and blade assembly according to the present invention.
FIG. 6 is an exploded perspective view of the blade assembly of FIG. 5.
FIG. 7 is a partial perspective view of the laryngoscope of FIG. 1 illustrating an interlocking mount on the handle for the blade assembly.

The width of supporting block 28 is chosen such that when mounted on the blade 22, the overall combined width will just fit between the spaced walls 34, shown in FIG. 7, of a corresponding mounting bracket 40. FIG. 7 shows a bracket 40 typically used on laryngoscope handles for receiving a laryngeal blade assembly. Bracket 40 can be sized to fit either a fiber optic or conventional, standard lamp type laryngeal blade assembly depending on the handle portion. As shown in FIGS. 1, 2 and 7 the sides of the bracket 40 are spaced apart in accordance with ASTM F965, ASTM F1195, ISO7376-1, ISO7376-3, and EN1819 standards to receive the assembly of blade 22 and supporting block 28.

Thus in operation the described laryngeal blade assembly 14 will smoothly and snugly fit into its corresponding bracket 40 when raised to the operative position of FIG. 2 and will force lamp 18 into contact with battery contact 19 to illuminate the lamp. Light from lamp 18 is then fed via optical fibers in light pipe 29 to the distal end of light pipe 29 to allow the desired target to be illuminated. With blade assembly 14 in the folded position of FIG. 1, the lamp 18 is de-energized.

FIGS. 5–7 illustrates a conventional, standard lamp type laryngoscope 50 with a traditional lamp 52 mounted in the distal end of a tube 54 which is in turn positioned in cavity 26 on blade 22. As noted, the major differences between the conventional laryngoscope and a laryngoscope having a fiber optic light pipe assembly are taught in previously incorporated U.S. Pat. No. 4,958,624 to Stone et al. According to the prior art, the handle of one type of laryngoscope is not physically or electrically interchangeable with the handle of the other type. However, the supporting blocks 28 and 58 of each type of light pipe assembly have bores 35 that are sized to fit blade 22 threaded portion 36, and screw assembly 30.

Tube 54 is part of conventional light pipe assembly 24 and is formed in the same approximate right angle configuration as light pipe 29. Tube 54 terminates proximally in block 58 at a flat contact 60. Lamp 52 is electrically connected by wire 62 within tube 54 to contact 60 for one side of the circuit and blade 22 provides the other side. When the blade assembly 14 is in the operative position of FIG. 5, the contact 60 engages a contact button 64 which is connected to a battery 21 and is spring urged to maintain contact therewith.

Supporting block 58 is similar in configuration to block 28 with similar bores 35, but slots 38 and 66, respectively, have different dimensions. As in the preceding, all major components are adequately sized in accordance with the above-mentioned standards.

Referring to FIG. 5, the upper portion of handle 70 has a mounting bracket similar to bracket 40 including a pair of spaced walls for accommodating the supporting block 58 and the blade 22 when assembled thereto. Slot 66 of supporting block 58 is designed to engage pin 72 and provide the necessary mutually exclusive attachment function with pin 72 of the handle 70.

Referring to FIGS. 3 and 9–13, the releasable mounting for the subject invention of the light pipe assembly to the blade will be described with respect to a laryngoscope having a fiber optic light pipe assembly. It should be understood that the following description also applies to the conventional, standard lamp type laryngoscope.

Figure 11:
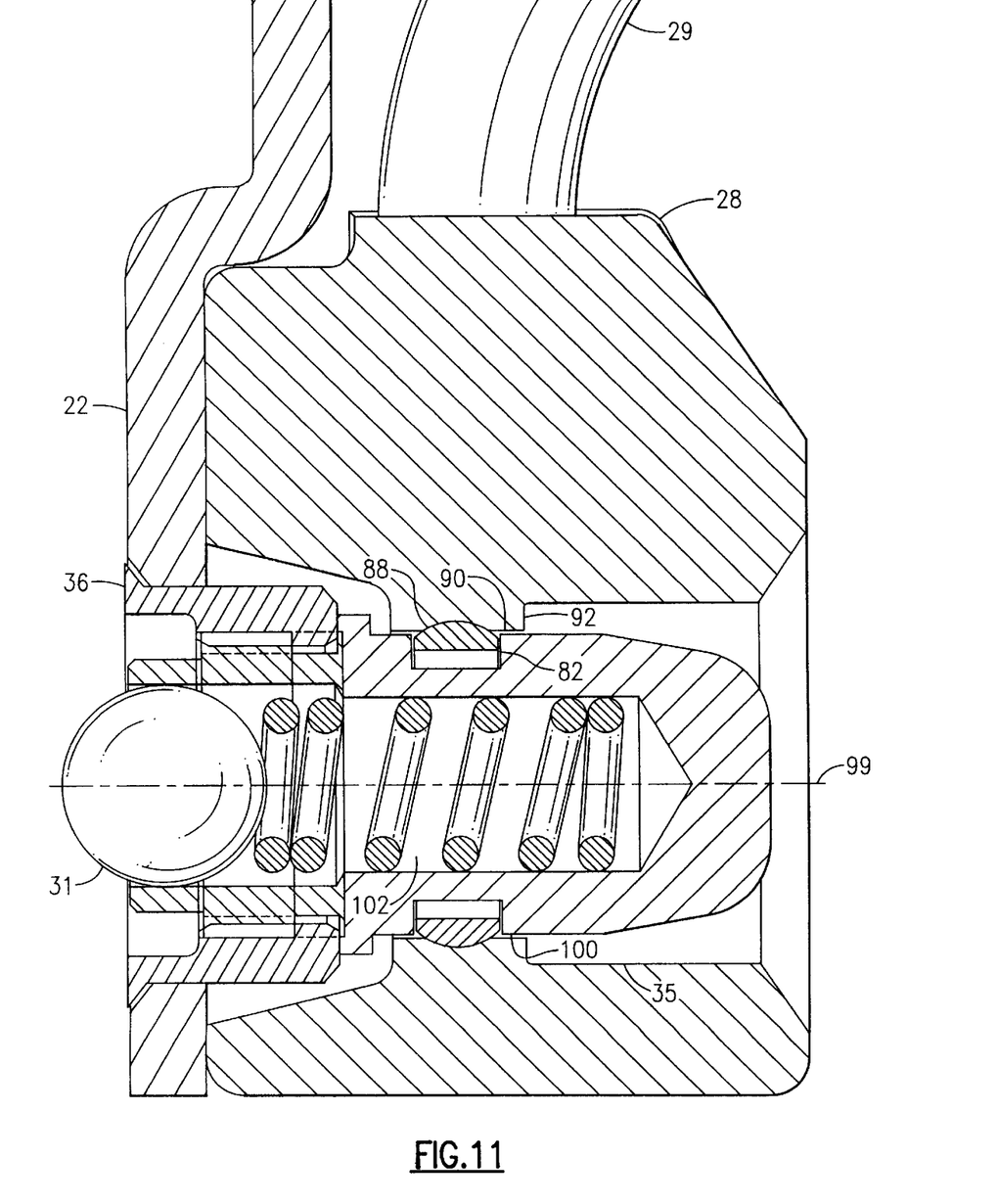
FIG. 11 is a partial enlarged cross sectional view of the laryngoscope of FIG. 3 and FIG. 6 depicting the mounting of the blade assembly in accordance with a third preferred embodiment.
Figure 12:
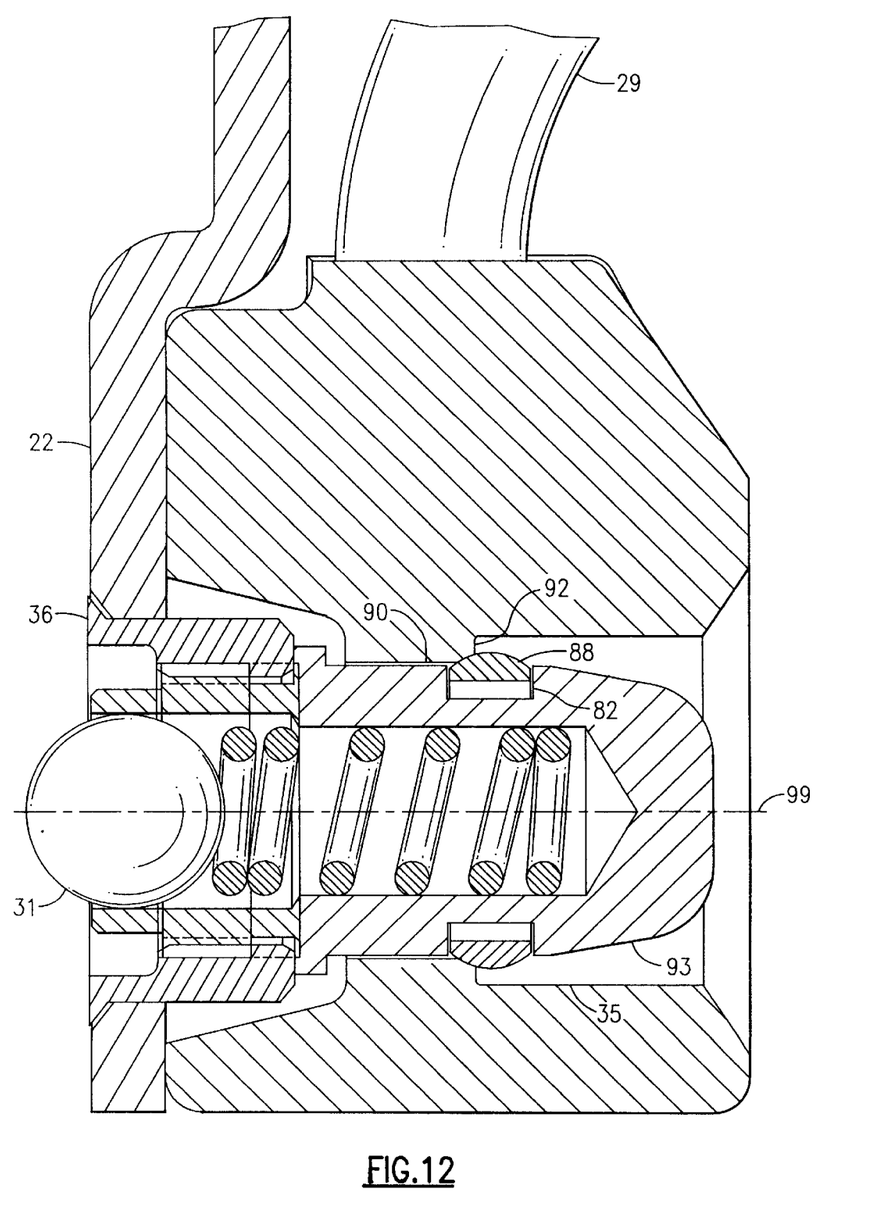
FIG. 12 is a partial enlarged cross sectional view of the laryngoscope of FIG. 3 and FIG. 6 depicting the mounting of the blade assembly in accordance with a fourth preferred embodiment.

The screw assembly 31 includes a mounting post 100 having a ball plunger 102. The mounting post 100 further includes a threaded portion 80 and an undercut portion 82, as well as an annular engagement member 84 which is fitted within the undercut portion 82, shown more clearly in FIGS. 3 and 9–13. The annular engagement member 84 shown in FIG. 3 can be any design that will allow secure engagement with internal boss 90, including an O-ring 86 (FIGS. 9, 10 and 13), and a split metal ring 88 (FIGS. 11, 12 and 14). Each of these embodiments will now be described separately.

Figure 9:
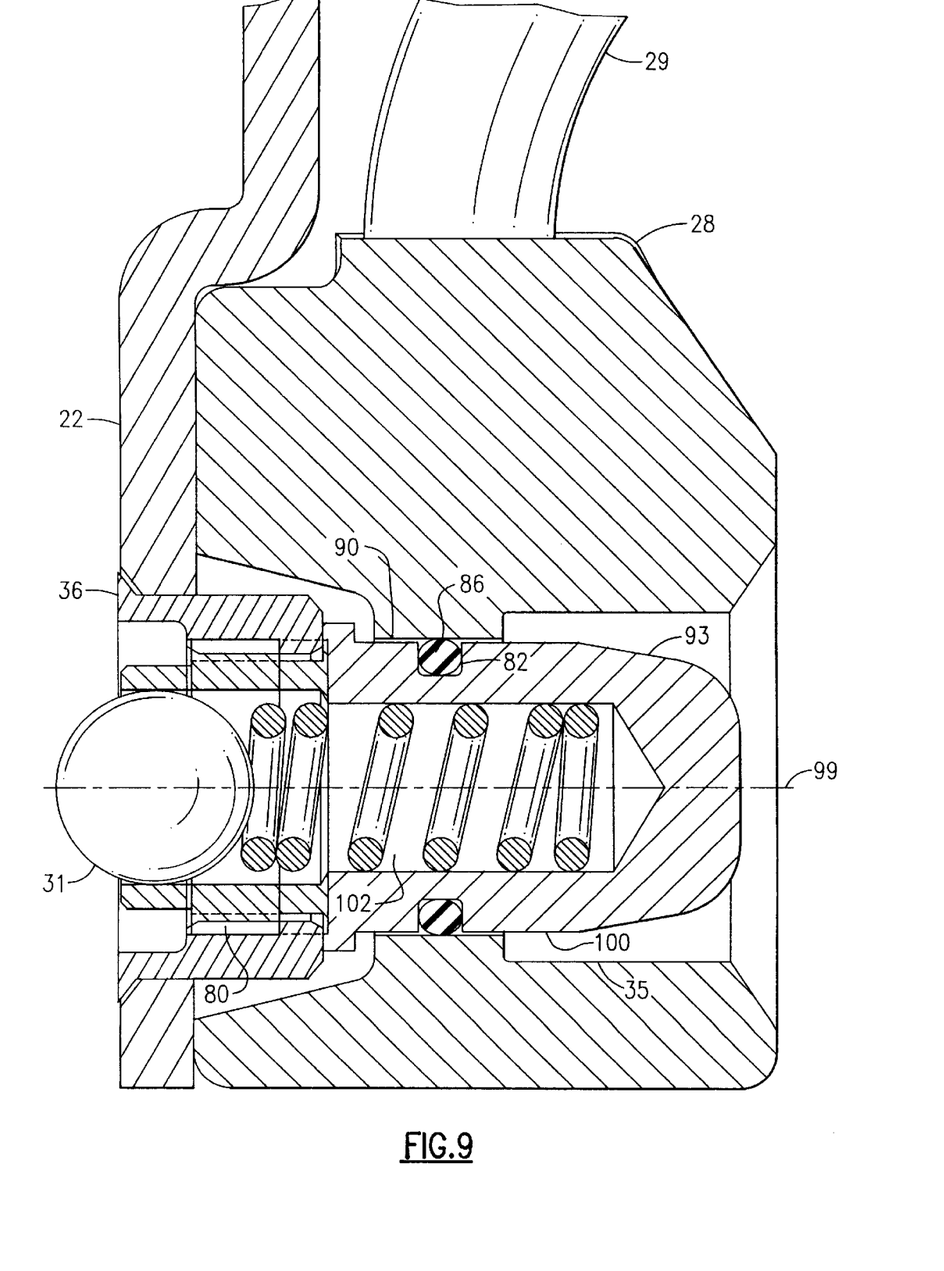
FIG. 9 is a partial enlarged cross sectional view of the laryngoscope of FIG. 3 and FIG. 6 depicting the mounting of the blade assembly in accordance with a first preferred embodiment.

Referring to FIG. 9, the O-ring 86 is slid over a ramped portion 93 of the mounting post 100 to be fitted within undercut portion 82. As supporting block 28 is positioned over assembly 31, the pressure exerted by the undersized portion of the bore 35 of supporting block 28 compresses the O-ring 86 retained in the undercut portion. This compression creates an interference fit wherein the O-ring 86 securely engages an internal boss 90 provided in bore 35 of supporting block 28 thereby creating an adequate holding force. On the other hand, the supporting block 28 is still easily removable along the axis 99 without the need for any tools when a release force sufficient to overcome the holding force is applied.

Figure 10:
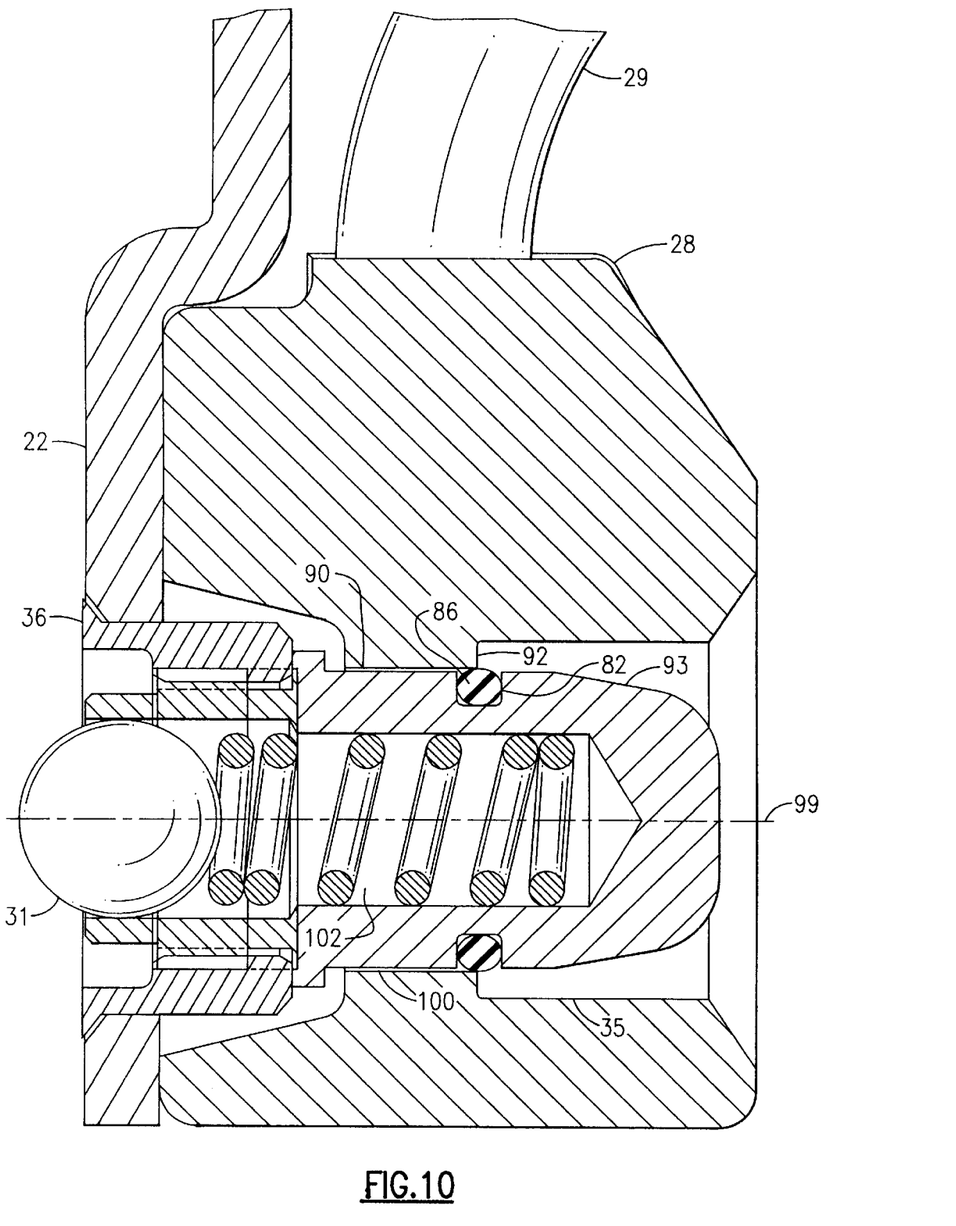
FIG. 10 is a partial enlarged cross sectional view of the laryngoscope of FIG. 3 and FIG. 6 depicting the mounting of the blade assembly in accordance with a second preferred embodiment.

According to an alternate embodiment shown in FIG. 10, the position of the undercut portion 82 can be varied so that the fitted O-ring 86 engages a shoulder 92 of the internal boss 90 thereby creating a detent arrangement. Similarly, the compression of the O-ring 86 by the internal boss 90 creates an interference fit that adequately holds the supporting block 28 onto the mounting post 100, while still allowing the supporting block 28 to be easily removed along the axis 99 without the need for any tools when the release force is applied.

Referring to FIGS. 11 and 14, a split metal ring 88 can be fitted within undercut portion 82. As the supporting block 28 is positioned over the screw assembly 30, the pressure exerted by the undersized portion of the bore 35 of supporting block 28 compresses the split metal ring 88 retained in the undercut portion. This compression creates an interference fit wherein the split metal ring 88 securely engages the internal boss 90 provided in the bore 35 of supporting block 28 thereby creating an adequate holding force. On the other hand, the supporting block 28 is still easily removable along the axis 99 without the need for any tools when a release force sufficient to overcome the holding force is applied.

In an alternate embodiment shown in FIG. 12, the position of the undercut portion 82 and the split metal ring 88 can be varied so that the split metal ring 88 engages the shoulder 92 of the internal boss 90 to create a snap-fitting arrangement similar to the detent arrangement shown in FIG. 10.

There are several advantages provided by using the split metal ring 88. First, split metal ring 88 provides for a more gradual contour for the supporting block 28 to slide over. O-ring 86 does not provide for the same gradual contour and, thus, is more susceptible to tearing. Second, a gap 110 (FIG. 14) in split metal ring 88 allows for cleaning access and for circumferential, and thereby radial, compression.

Figure 13:
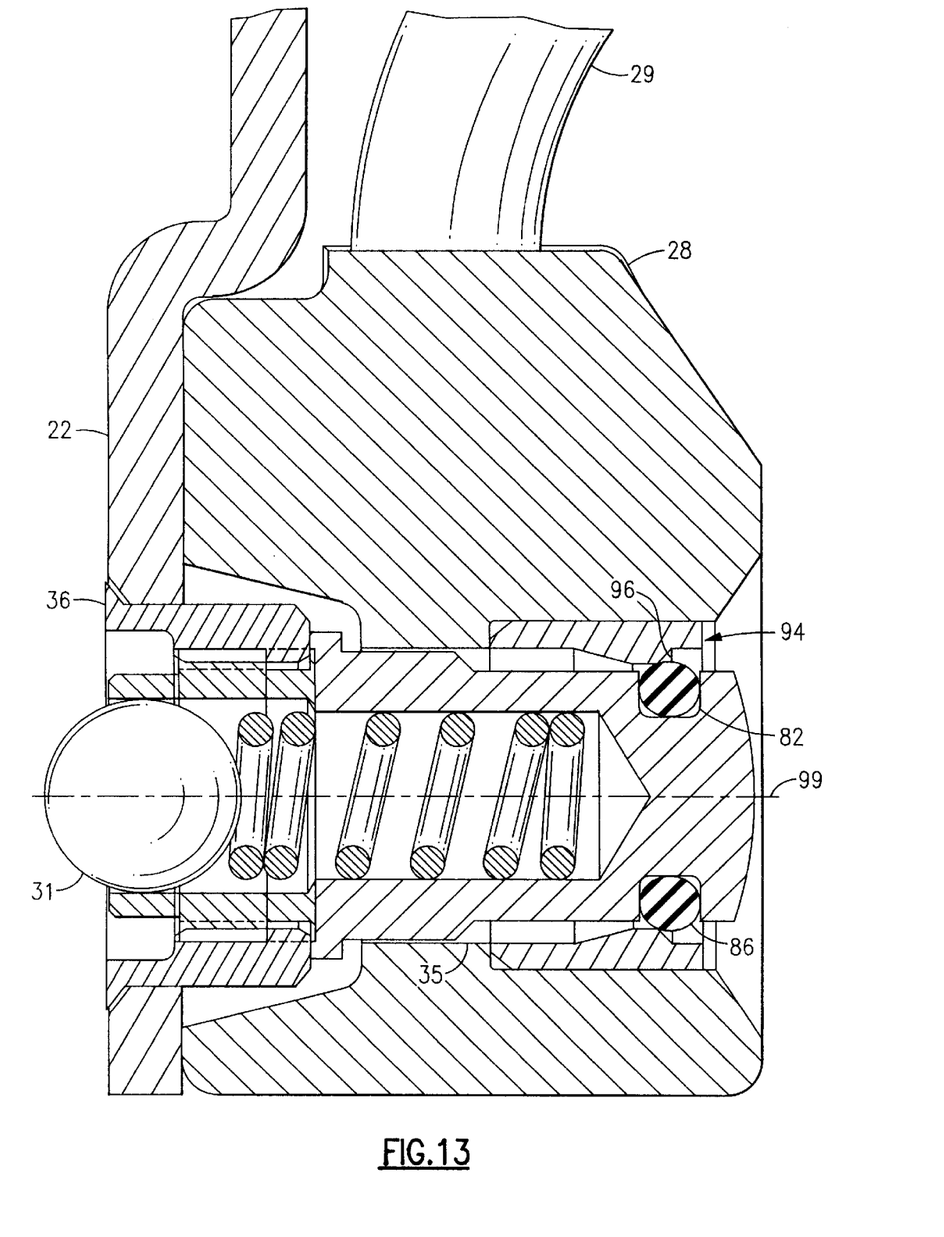
FIG. 13 is a partial enlarged cross sectional view of the laryngoscope of FIG. 3 and FIG. 6 depicting the mounting of the blade assembly in accordance with a fifth preferred embodiment.
Figure 14:
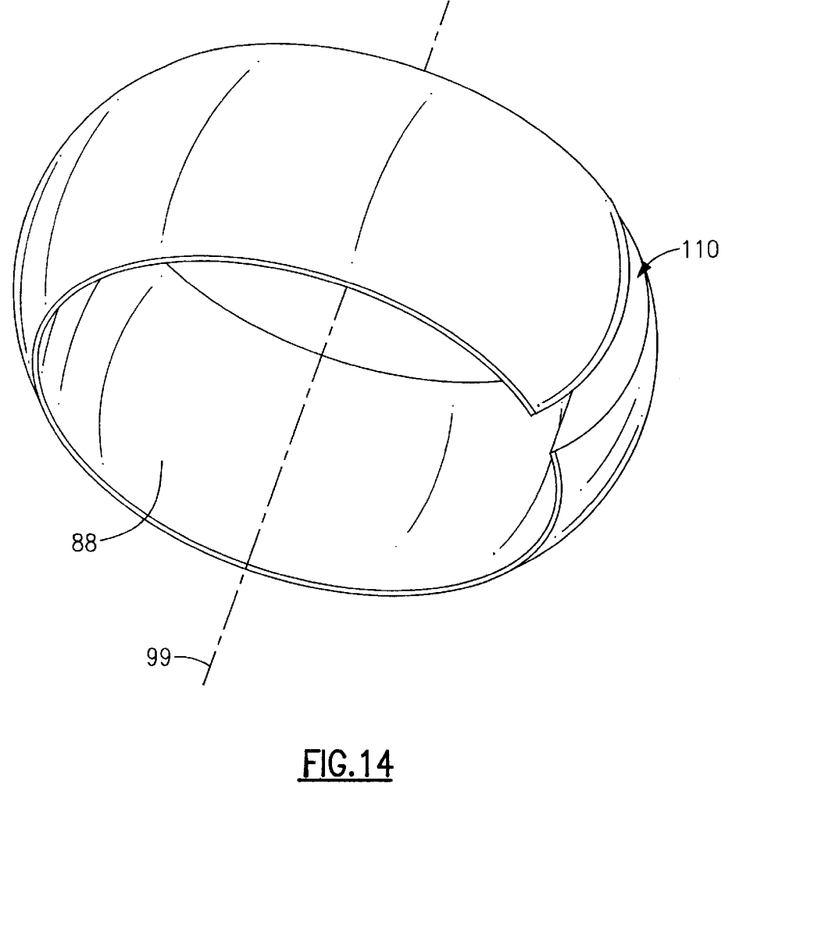
FIG. 14 is a perspective view of a split metal ring used in conjunction with the preferred embodiments of FIGS. 11–12.

In the embodiment shown in FIG. 13, an annular sleeve 94 can be provided inside of bore 35 for engaging O-ring 86 or any other annular engagement member. The annular sleeve 94 is provided with a shoulder 96 for engaging O-ring 86. As in the preceding, the compression of the O-ring 86 creates an interference fit to secure an adequate holding force. Further, as shown in FIG. 13, the undercut portion 82 is positioned so that the O-ring 86 will engage the shoulder 96 of the annular sleeve 94. There are several advantages provided by using annular sleeve 94 with shoulder 96. First, an independent separately fabricated sleeve allows for a distinct and finer finish to be added to the surface of shoulder 96, without the need or expense of adding a fine finish to any other surfaces or bores in sleeve 94 or supporting block 28. The finer finish provides for a smoother contact surface on shoulder 96 for O-ring 86 as it travels into engagement position, thereby prolonging the life of the O-ring.

Second, an independent separately fabricated sleeve allows for the location and configuration of the shoulder 96 to be optimized for best stability and retaining strength when O-ring 86 is in engagement position.

While these combination of components are shown in several embodiments, the combinations are not limited to those embodiments shown. It should be apparent to one skilled in the art that the position of the undercut portion 82 could easily be adjusted along the axial direction of the shaft, similarly different annular engagement members 84, or various configurations or modifications of the bore can create a varied number of combinations.

After using laryngoscope 10, the blade 22 and the light pipe assembly 24 must be sanitized, therefore, requiring removal of the light pipe assembly 24 from the blade 22. In the present invention, the light pipe assembly 24 can easily be released from the blade 22 by overcoming the interference fit between the supporting block 28 and the screw assembly 31.

Although this invention has been described with reference to a number of embodiments, it should be recognized that the invention is not limited to those embodiments shown. Rather, many modifications and variations would present themselves to those of skill in the art without departing from the scope and spirit of this invention, as defined in the appended claims.

We claim:

1. A blade assembly for a laryngoscope, said blade assembly comprising:

a laryngeal blade configured for viewing the larynx of a patient;

a light pipe assembly attached to said blade such that a light pipe is disposed alone a major dimension of said blade; and means for releasably attaching said light pipe assembly to said blade, said means being disposed in a non-axial direction in relation to said major dimension, wherein said light pipe assembly can be released from said blade along said non-axial direction without the aid of tools;

wherein said light pipe assembly includes a supporting block for fixedly retaining said light pipe, said block having a bore disposed in a non-axial direction to said major dimension, and in which said releasable attachment means includes:

a non-axial member fixedly attached to said blade and sized for engaging said bore, said non-axial member including a shaft having an undercut portion; and an annular engagement member fitted within said undercut portion for engaging said bore to allow release of said light pipe assembly when a predetermined release force applied along the axis of said bore is exceeded.

2. The blade assembly of claim 1, wherein said annular engagement member is selected from the group consisting of a split ring, and an O-ring.

3. The blade assembly of claim 1, wherein said bore includes an internal boss for engaging said annular engagement member.

4. The blade assembly of claim 1, wherein said bore includes an annular sleeve for engaging said annular engagement member.

5. A hand-held laryngoscope for the examination of the larynx said laryngoscope comprising:

a handle;

a laryngeal blade attached to said handle;

a light pipe assembly attached to said blade such that a light pipe is disposed alone a major dimension of said blade; and means for releasably attaching said light pipe assembly to said blade, said means being disposed in a non-axial direction in relation to said major dimension, wherein said light pipe assembly can be released from said blade along said non-axial direction without the aid of tools, wherein said light pipe assembly includes a supporting block for fixedly retaining said light pipe, said block having a bore disposed in a non-axial direction to said major dimension, and in which said releasable attachment means includes:

a non-axial member fixedly attached to said blade and sized for engaging said bore, said non-axial member including a shaft having an undercut portion; and an annular engagement member fitted within said undercut portion for engaging said bore to allow release of said light pipe assembly when a predetermined release force applied along the axis of said bore is exceeded.

6. The laryngoscope of claim 5, wherein said annular engagement member is selected from the group consisting of a split ring, and an O-ring.

7. The laryngoscope of claim 5, wherein said bore includes an internal boss for engaging said annular engagement member.

8. The laryngoscope of claim 5, wherein said bore includes an annular sleeve for engaging said annular engagement member.

9. The laryngoscope of claim 5, wherein said handle includes a light source.

10. In a set of non-interchangeable type light laryngoscopes that have a first handle and a second handle, and a removable blade assembly with mutually exclusive interlocking mounting mechanisms, the combination of:

a laryngeal blade configured for viewing the larynx of a patient, said laryngeal blade being attachable to either of said handles;

a first type light pipe assembly which can be attached to said blade, said first type light pipe assembly having a first light pipe which when attached extends along a major dimension of said blade;

a second type light pipe assembly which can be attached to said blade, said second type light pipe assembly having a second light pipe which when attached extends along a major dimension of said blade; and means for releasably attaching either of said light pipe assemblies to said blade, said means being disposed in a non-axial direction in relation to said major dimension wherein either of said light pipes can be released from said blade along said non-axial direction without the aid of tools.

11. The laryngoscope set of claim 10, wherein both of light pipe assemblies includes a supporting block for fixedly retaining said either of said light pipes, said block having a bore disposed in a non-axial direction to said major dimension, and in which said releasable attachment means includes:

a non-axial member fixedly attached to said blade and sized for engaging said bore, said non-axial member including a shaft having an undercut portion; and an annular engagement member fitted within said undercut portion for engaging said bore to allow release of either of said light pipe assemblies when a predetermined release force applied along the axis of said bore is exceeded.

12. The laryngoscope set of claim 11, wherein said annular engagement member is selected from the group consisting of a split ring, and an O-ring.

13. The laryngoscope set of claim 11, wherein said bore includes an internal boss for engaging said annular engagement member.

14. The laryngoscope set of claim 11, wherein said bore includes an annular sleeve for engaging said annular engagement member.

15. The laryngoscope set of claim 11, wherein said handle includes a light source.

16. The laryngoscopes set of claim 10, further including first and second type removable blade assemblies, such that when said blade is secured to said first type light pipe assembly a first type removable blade assembly is provided and when said blade is secured to said second type light pipe assembly a second type removable blade assembly is provided.

* * * * *

UNITED STATES PATENT AND TRADEMARK OFFICE
CERTIFICATE OF CORRECTION

PATENT NO. : 6,013,026
DATED : January 11, 2000
INVENTOR(S) : Krauter et al.

It is certified that error appears in the above-identified patent and that said Letters Patent is hereby corrected as shown below:

On the Title page, item [54] Title:

After the word ASSEMBLY please delete [AND SET OF LARYNGOSCOPES.

Signed and Sealed this

Eighth Day of August, 2000

Attest:

Attesting Officer

Q. TODD DICKINSON
Director of Patents and Trademarks